United States Patent [19]
Nagano et al.

[11] Patent Number: 5,424,216
[45] Date of Patent: Jun. 13, 1995

[54] NO RADICAL MEASURING METHOD AND APPARATUS

[75] Inventors: Tetsuo Nagano; Kazuya Kikuchi; Masaaki Hirobe; Hiroshi Hayakawa; Yasunobu Hirata; Tsuneaki Sugimoto, all of Tokyo; Sakae Higashidate, Hachioji, all of Japan

[73] Assignees: Jasco Corporation, Hachioji; Masaaki Hirobe, Tokyo, both of Japan

[21] Appl. No.: 106,705

[22] Filed: Aug. 16, 1993

[51] Int. Cl.⁶ ............... G01N 21/76; G01N 21/78
[52] U.S. Cl. ................................. 436/116; 436/172; 436/805; 422/52
[58] Field of Search ............... 436/116, 172, 805; 422/52

[56] References Cited

U.S. PATENT DOCUMENTS

| | | | |
|---|---|---|---|
| 3,659,100 | 4/1972 | Anderson et al. | 250/71 R |
| 4,737,455 | 4/1988 | De Baetselier | 435/7 |
| 4,765,961 | 8/1988 | Schift et al. | 422/52 |
| 4,863,689 | 9/1989 | Leong et al. | 422/52 |
| 4,916,077 | 4/1990 | Forster et al. | 436/160 |
| 5,015,590 | 5/1991 | Kinrade | 436/117 |
| 5,171,668 | 12/1992 | Sugiyama | 435/28 |
| 5,275,956 | 1/1994 | Bansho et al. | 436/125 |

Primary Examiner—Timothy M. McMahon
Assistant Examiner—N. Bhat
Attorney, Agent, or Firm—Ronald R. Snider

[57] ABSTRACT

An NO radical measuring method comprising the steps of mixing a test sample solution containing NO radicals with hydrogen peroxide or an analogous substance thereto and luminol or an analogous substance thereto, and measuring the intensity of chemiluminescence. The method enables a trace amount of NO radical to be measured with accuracy and in real time. An apparatus used for this method is also disclosed.

14 Claims, 5 Drawing Sheets

NO RADICAL MEASURING METHOD AND APPARATUS

FIELD OF THE INVENTION

The present invention relates to an NO radical measuring method and apparatus and, more particularly, to an NO radical measuring method and apparatus which utilizes chemiluminescence.

DESCRIPTION OF THE RELATED ART

NO radicals act an as a signal transmitter substance with respect to the vascular endothelium, central and peripheralneurons and phagocytic cells, and they are considered to be a new autacoid. To elucidate a correlation between the amount of NO and blood pressure, for example, how NO radicals function in a living body as a pressure controller and whether or not NO radicals are a systemic controller is the most fundamental to the prevention of and remedy for cardiovascular diseases.

To grasp the dynamic change of NO radicals in the body in real time is particularly important in medicine and pharmacy from the point of view of the elucidation of the mechanism of vascular diseases.

The following five methods are conventionally known as a method of detecting NO radicals.

(1) A chemiluminescence detecting method using ozone
(2) A detecting method utilizing gas chromatography-mass sepctrometry (GC-MS)
(3) A detecting method utilizing ESR
(4) An absorbance measuring method utilizing a Griese reaction
(5) An absorbance measuring method using oxyhemoglobin.

The conventional method (1) is a method of measuring NO radicals in the atmosphere with a high sensitivity. However, this method is possible only in a gaseous phase, so that a complicated and drastic after treatment is necessary when it is applied to an organ. In addition, measurement in real time is impossible by the method (1).

The conventional method (2) is known as a method of identifying the production of NO radicals from a macrophage. However, it is also impossible to measure the dynamic change in the amount of NO radical by this method.

The detection sensitivity of the conventional method (3) is about $10^{-7}$M, so that it is very difficult to use this method for ultramicroanalysis in an organ.

The conventional methods (4) and (5) are now generally used by pharmacologists, biochemists and medical scientists. However, the limit of detection of the absorbance measuring method based on the principle of the measurement in the methods (4) and (5) is $10^{-7}$ to $10^{-8}$M, and it is substantially impossible to quantitatively determine NO radicals in an organ with high reliability which acts as a second messenger.

In addition, NO radicals are known to be unstable in physiological solutions and to be easily oxidized to nitrite ions and nitrate ions, so that it is necessary to measure the amount of NO radical immediately after a sample solution is extracted from an organ.

Therefore, both of the methods (4) and (5) are usable only in the case in which a considerable amount of NO radical is produced, for example, from a cultured cell and a macrophage.

For this reason, development of a method of measuring NO radicals with a very high sensitivity is strongly demanded.

SUMMARY OF THE INVENTION

Accordingly, it is an object of the present invention to eliminate the above-described problems in the related art and to provide a method of measuring NO radicals with a very high sensitivity and an apparatus used for the method.

As a result of studies undertaken by the present inventors so as to achieve this aim, it has been found that it is possible to measure NO radicals with a high sensitivity ($10^{-12}$ to $10^{-15}$M) by a chemiluminescence system which is obtained by adding hydrogen peroxide or an analogous substance thereto to a chemiluminescence agent. On the basis of this finding, the present invention has been achieved.

In a first aspect of the present invention, there is provided an NO radical measuring method comprising the steps of mixing sample solution containing NO radicals with hydrogen peroxide or an analogous substance thereto and luminol or an analogous substance thereto, and measuring the intensity of chemiluminescence.

In a second aspect of the present invention, there is provided an NO radical measuring apparatus comprising a flow cell into which a sample solution containing NO radicals and a mixed solution containing hydrogen peroxide or an analogous substance thereto and luminol or an analogous substance thereto are introduced, and a luminescence detecting portion disposed opposite to the flow cell.

As examples of the analogous substance to luminol in the present invention will be cited isoluminol, AHEI, ABEI, ABEI-NCS, luciferin, Cypridina luciferin, CLA and MCLA. In the case of using luminol, the concentration thereof in the mixed solution is 10 nM to 10 mM, preferably 1 $\mu$M to 1 mM.

As examples of the analogous substance to hydrogen peroxide in the present invention will be cited a system which produces hydrogen peroxide such as (xanthine and xanthine oxidase) and tert-butylhydroperoxide. In the case of using hydrogen peroxide, the concentration thereof in the mixed solution is preferably about 1 $\mu$M to 100 mM.

The pH of a luminol-hydrogen peroxide reaction system is preferably not less than 7. When a perfusate in an organ such as a kidney is an object of measurement, the pH of the reaction system is preferably about 12.

The above and other objects, features and advantages of the present invention will become clear from the following description of the preferred embodiments thereof, taken in conjunction with the accompanying drawings.

DESCRIPTION OF THE PREFERRED EMBODIMENTS

Preferred embodiments of the present invention will be explained hereinunder with reference to the accompanying drawings.

EXAMPLE 1

Chemiluminescence Detecting Method for Measuring NO Radical by Luminol+Hydrogen Peroxide ($H_2O_2$) System $H_2O_2$ is added to luminol which is dissolved in an aqueous $K_2CO_3$ solution, an aqueous NO radical solution is added to the mixture, and the intensity of chemiluminescence is measured by a chamber type chemiluminescence detector.

An aqueous $K_2CO_3$ having a concentration of 125 mM was added to luminol which is dissolved in an aqueous $K_2CO_3$ so that the final concentration of luminol was 12.5 $\mu$M. An aqueous solution of $H_2O_2$ having a concentration of 62.5 mM was further added to the mixture so that the concentration of $H_2O_2$ was 400 $\mu$M.

The mixture was charged into a chamber type chemiluminescence detector and stirred. 100 $\mu$l of aqueous radical NO solutions having various concentrations were added to the mixture so as to measure their chemiluminescence intensities.

The same test was carried out on the mixture with no NO added thereto, an aqueous $NaNO_2$ solution and an aqueous $NaNO_3$ solution.

Figure 1:
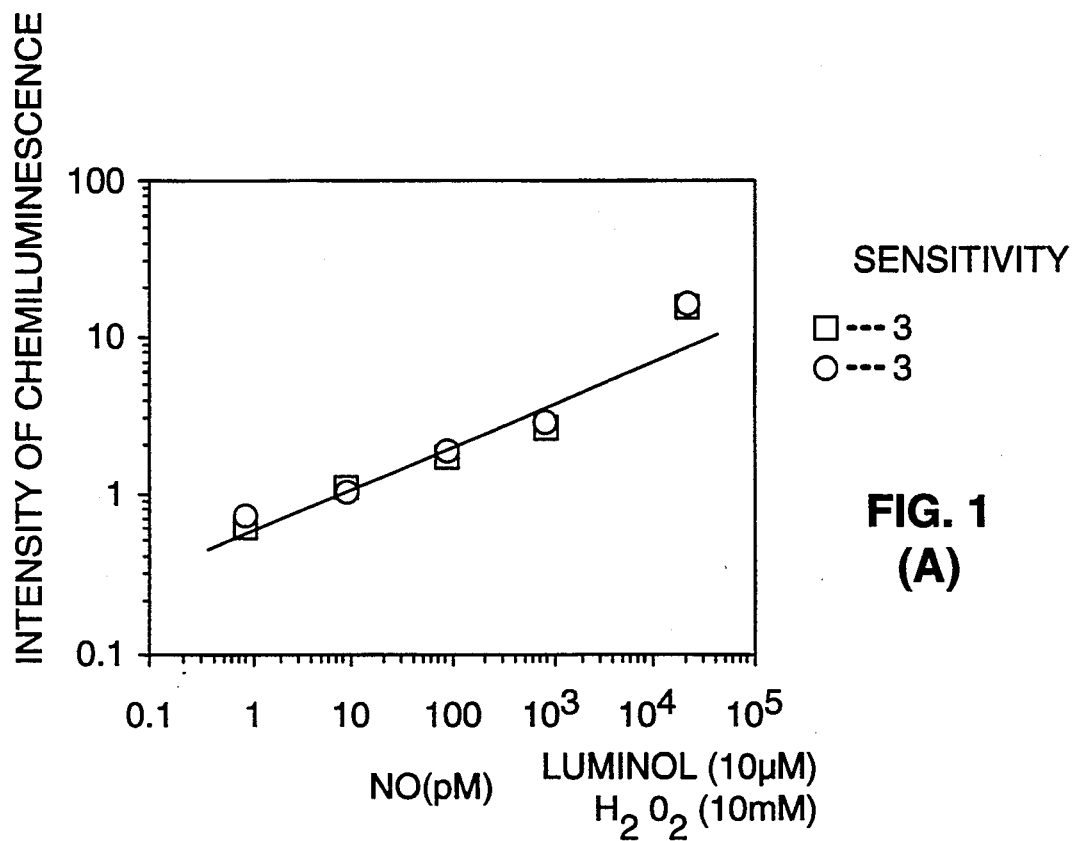
FIG. 1 is an explanatory view of an example of measurement by an embodiment of an NO radical measuring method according to the present invention.
Figure 1:
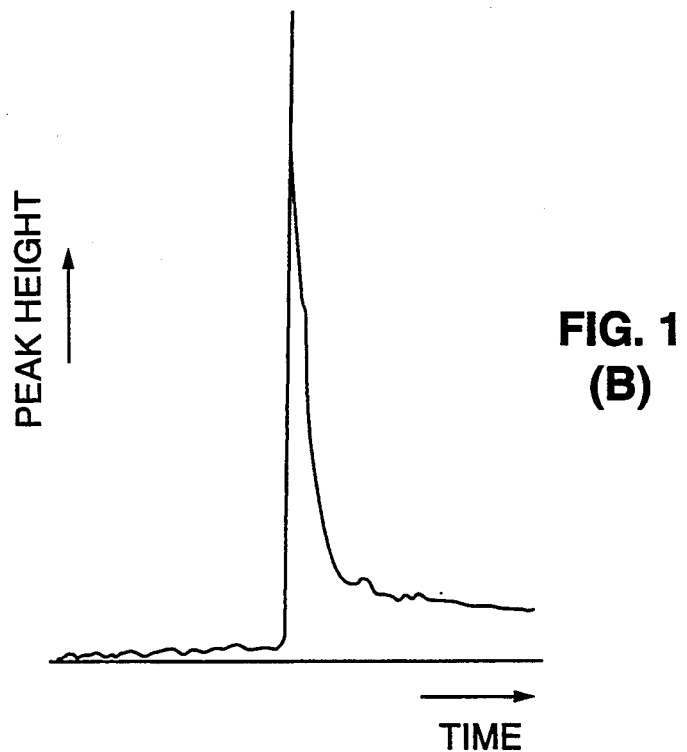

The results are shown in FIG. 1.

From FIG. 1(A), it is observed that the chemiluminescence intensity linearly increases in proportion to the amount of NO radical.

FIG. 1(B) shows that the peak width of the chemiluminescence intensity is small, which suggests that this method is suitable for continuous measurement or measurement in the state of flow.

EXAMPLE 2

Figure 2:
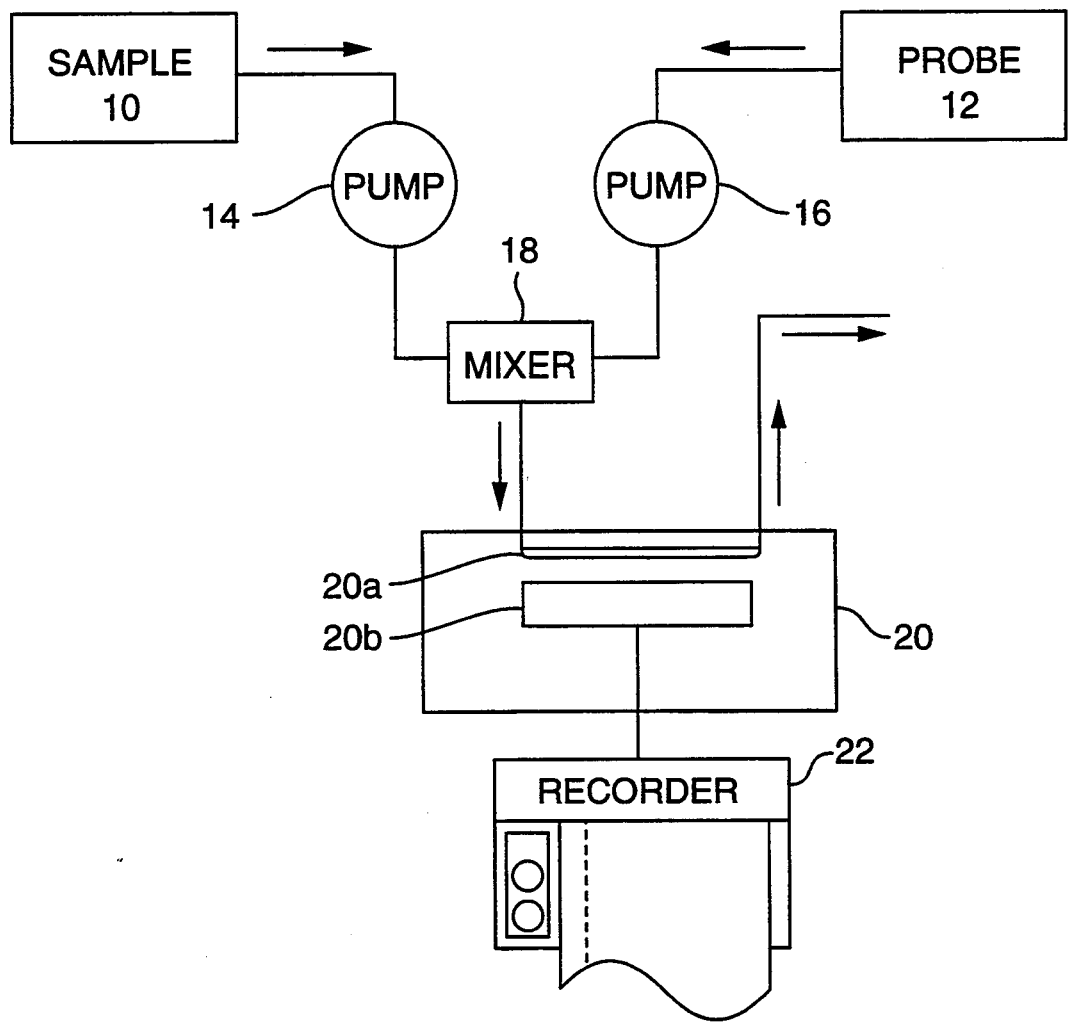
FIG. 2 is an explanatory view of the schematic structure of an embodiment of an NO radical measuring apparatus according to the present invention.

Quantitative Determination of NO Radical by Luminol+Hydrogen Peroxide ($H_2O_2$) System Using Flow System Measurement of NO radicals by a flow system such as that shown in FIG. 2 was attempted.

In the measuring apparatus shown in FIG. 2, a predetermined amount of test sample solution 10 and a predetermined amount of chemiluminescence probe 12 are dilivered by pumps 14 and 16 respectively, and after they are mixed by a mixer 18, the mixture is introduced into a chemiluminescence detector 20. The chemiluminescence detector 20 is provided with a flow cell 20a having a spiral shape, for example, and a luminescence detector 20b which is disposed opposite to the flow cell 20a. The luminescence produced by reaction in the flow cell 20a is detected by the luminescence detector 20b. The result of the measurement of the intensity of chemiluminescence is recorded on a recorder 22.

In this example, an aqueous $K_2CO_3$ solution of luminol is added to distilled water with desferral (desferrioxamine) and $H_2O_2$ dissolved therein, thereby producing a chemiluminescence probe. Desferral acts as a metal remover and displays a background value lowering effect.

Apart from the solution, a phosphate buffer is degassed and NO radical gas is passed thereinto to prepare an aqueous NO radical solution (NO radicals-containing buffer).

Both solutions are mixed by the apparatus shown in FIG. 2, and the intensity of the chemiluminescence produced is measured by the chemiluminescence detector 20 equipped with the flow cell.

1 ml of an 400 mM aqueous $K_2CO_3$ solution of luminol having a concentration of 3.6 mM was added to 99 ml of an aqueous desferral solution having a concentration of 300 $\mu$M. 100 ml of an aqueous solution of $H_2O_2$ having a concentration of 20 mM was added to the mixture, and the resultant mixture was stirred to produce a chemiluminescence probe.

An NO radicals-containing buffer having a NO concentration of 20 pM was prepared by passing NO gas into a phosphate buffer having a concentration of 20 mM.

0.5 ml/min of the chemiluminescence probe was mixed with 2 ml/min of the NO radicals-containing buffer, and the intensity of the chemiluminescence produced was measured by the chemiluminescence detector 20 equipped with the flow cell.

Figure 3:
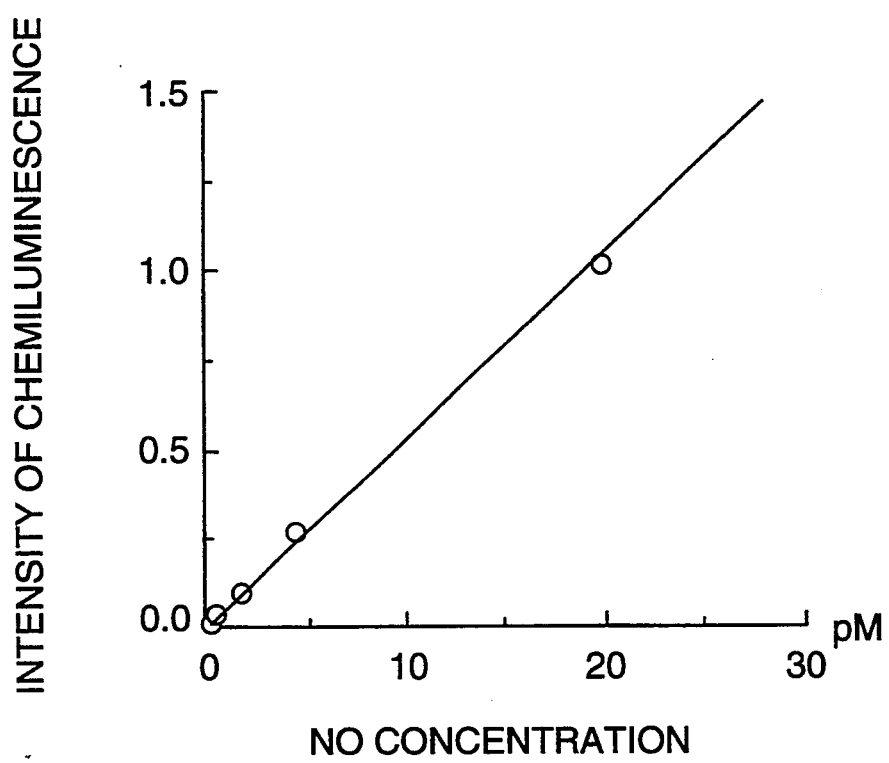
FIG. 3 explains the relationship between the NO radical concentration and the intensity of chemiluminescence observed when the apparatus shown in FIG. 2 is used.

As shown in FIG. 3 which shows the result, a linear relationship was observed between the NO concentration (100 fM to 10 $\mu$M) and the chemiluminescence intensity.

EXAMPLE 3

Figure 4:
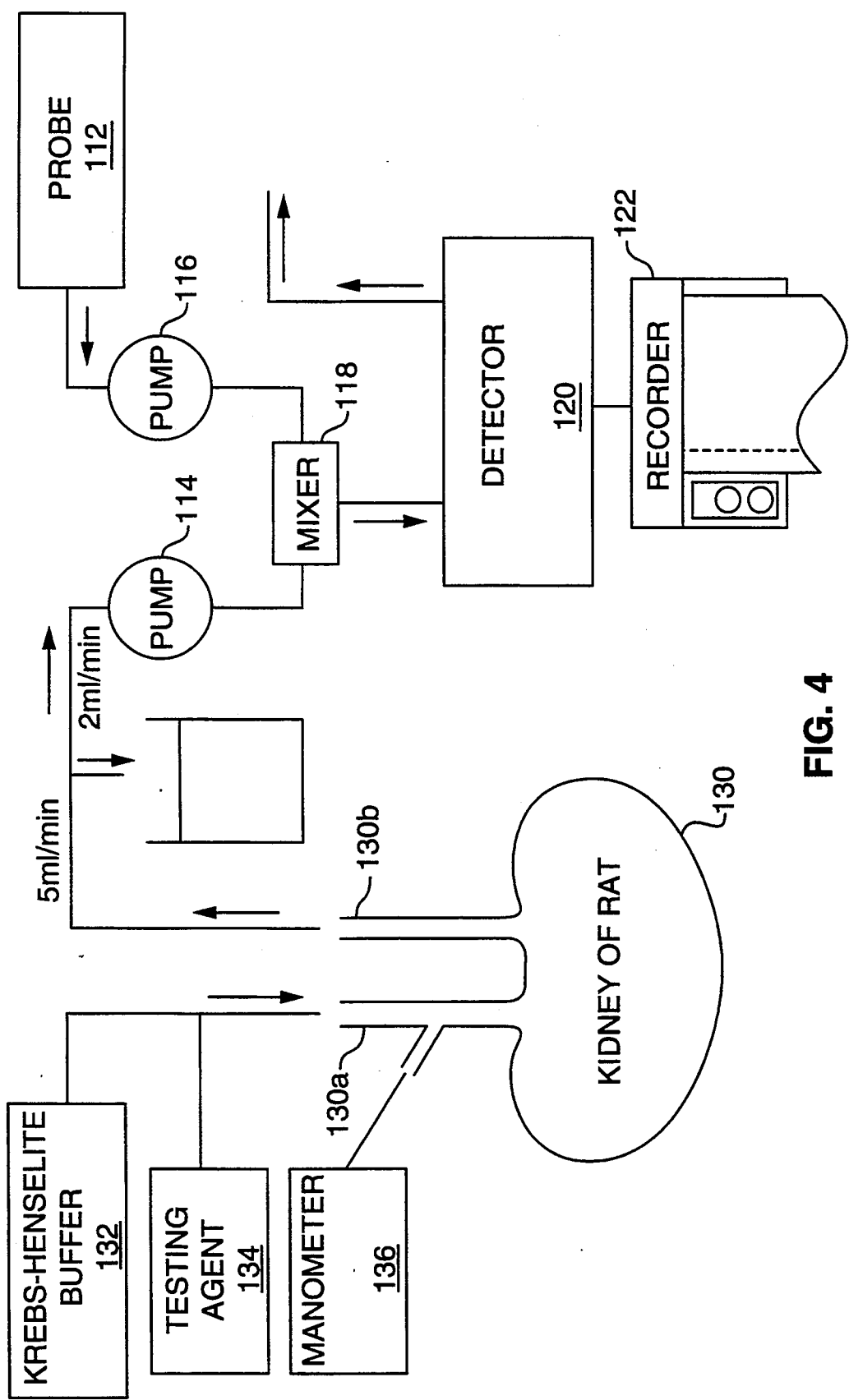
FIG. 4 is an explanatory view of the schematic structure of another embodiment of an NO radical measuring apparatus according to the present invention which is used for quantitative determination of the NO radical in a perfusate in an isolated kidney of rat.
Figure 5:
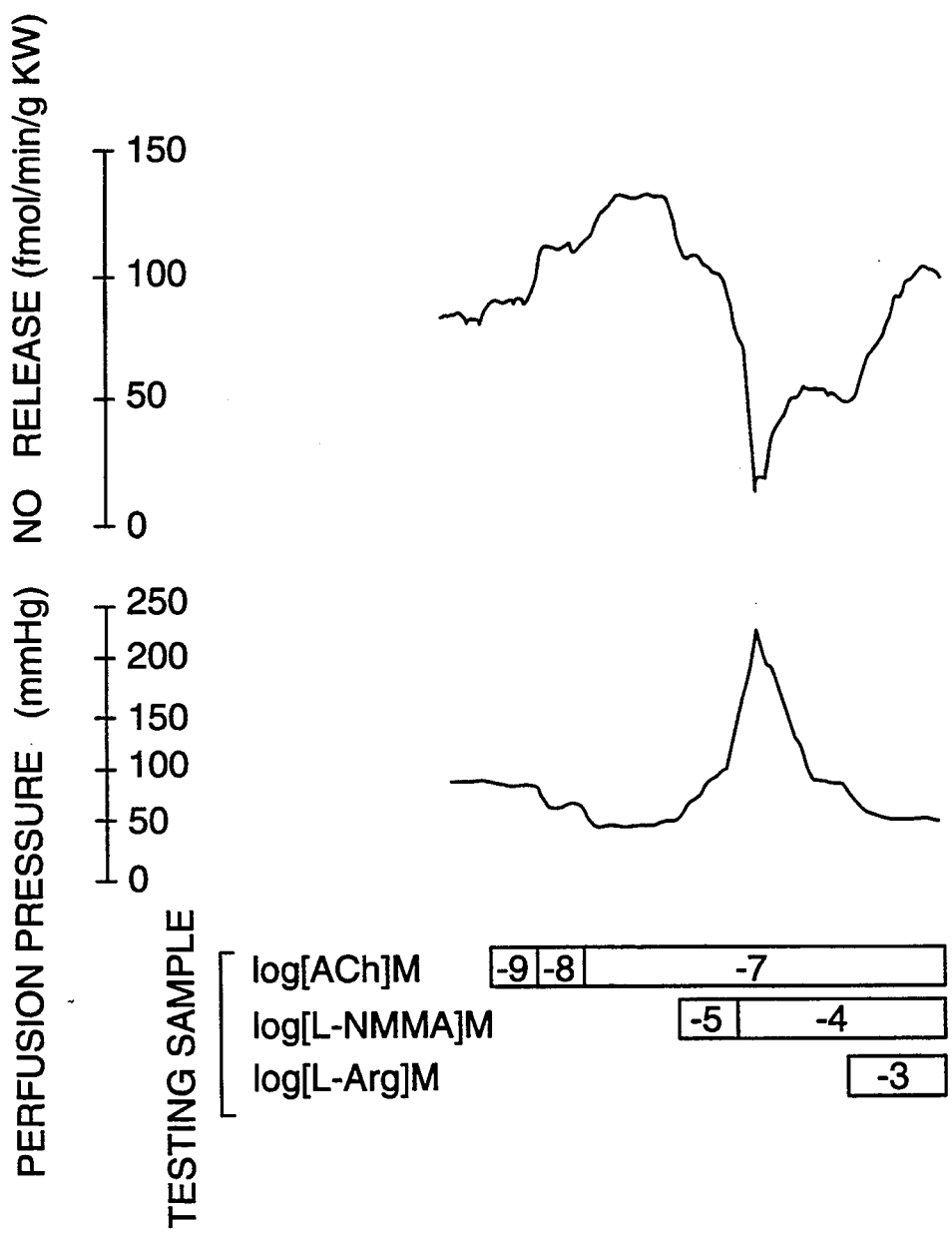
FIG. 5 explains the relationship between the NO radicals measured by the apparatus shown in FIG. 4 and the pressure of the perfusate.

Detection and Quantitative Determination of NO radical in Perfusate in Isolated Kidney of Rat by Luminol+Hydrogen Peroxide ($H_2O_2$) System Using Flow System FIG. 4 shows a system for measuring NO radicals in a perfusate in an isolated kidney of a rat. The elements which correspond to those shown in FIG. 2 are indicated by the same numeral prefixed by the numeral 1, and explanation thereof will be omitted.

As is obvious from FIG. 4, a Krebs-Henselite buffer 132 and a testing agent (kindney nephrovasostimulant) 134 are introduced into the artery 130a of a kidney 130 of a rat, and the pressure of the perfusion is monitored by a manometer 136.

5 ml/min, for example, of a perfusate is extracted from the vein 130b of the rat kidney 130, and only 2 ml/min of the perfusate was introduced into the measuring system by a pump 114.

By using this system, the NO radicals were detected and quantitatively determined from a kidney isolated from a Wistar-Kyoto(WKY) rat.

A chemiluminescence probe 112 was prepared by the method shown in Example 2.

The perfusate was passed through the artery 130a of the kidney 130 and the perfusate flowing out of the vein 130b was mixed with the chemiluminescence probe 112 through pumps 114 and 116, respectively. The mixture was introduced into a detector 120.

A perfusate (Krebs-Heselite buffer: 118 mM of NaCl, 4.7 mM of KCl, 2.5 mM of $CaCl_2$, 1.2 mM of $MgSO_4$, 1.2 mM of $KH_2PO_4$, 25 mM of $NaHCO_3$, and 11.1 mM of glucose) was first passed through the artery 130a for 5 minutes and thereafter a urokinase solution dissolved in the Krebs-Heselite buffer was perfused at a rate of 3000 U/H. The urokinase acts as a fibrinolytic agent. If no fibrinolytic agent is added, the base line changes with time, thereby making the measurement difficult.

The Krebs-Heselite buffer was then passed through the artery 130a for 10 minutes more, and $10^{-9}$M, $10^{-8}$M or $10^{-7}$M of acetylcholine, $10^{-5}$M or $10^{-4}$M of NG-monomethyl-L-arginine (L-NMMA) as an NO synthesis inhibitor, and $10^{-3}$M of L-arginine (L-Arg) (testing agent 134) were administered to the rat at a predetermined interval.

2 ml/min of the perfusate was mixed with 0.5 ml/min of the chemiluminescence prove 112, and the chemiluminescence intensity was measured by the chemiluminescence detector 120 equipped with the flow cell.

As a result, the detection of NO and a change in the pressure of the perfusion were simultaneously observed in real time. The increase or decrease of NO and the change in the pressure of the perfusion had an accurate and inverse correlation, and the effect of L-NMMA proves the selectivity of this measuring method.

As described above, according to the NO radical measuring method and apparatus of the present invention, since a test sample solution is mixed with hydrogen peroxide or an analogous substance thereto and luminol or an analogous substance thereto, and the intensity of chemiluminescence is measured, it is possible to measure a trace amount of NO radical with accuracy and in real time.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An NO radical measuring method comprising the steps of:
   mixing a sample aqueous solution containing NO radicals with a luminol hydrogen peroxide reaction system produced by mixing a solution selected from the group consisting of xanthine and xanthine oxidase, tert-butyl-hydroperoxide and hydrogen peroxide thereto and a material selected from the group consisting of isoluminol, AHEI, ABEI, ABEI-NCS, luciferin, Cypridina luciferin, CLA and MCLA and luminol and;
   measuring the intensity of chemiluminescence to directly measure NO radicals in said aqueous solution wherein the presence of chemiluminescence is an indication of NO radical and the absence of chemiluminescence indicates no NO radical.

2. An NO radical measuring method according to claim 1, wherein luminol concentration in said reaction system is 10 nM to 10 mM.

3. An NO radical measuring method according to claim 1, wherein an aqueous hydrogen peroxide solution is used for said luminol-hydrogen peroxide reaction system and the concentration thereof in said reaction system is 1 µM to 100 mM.

4. An NO radical measuring method according to claim 1, wherein the pH of said luminol-hydrogen peroxide reaction system is not less than 7.

5. An NO radical measuring method according to claim 1, wherein said measurement method is for a perfusate in an organ and said luminol-hydrogen peroxide reaction system pH is 7 to 12.

6. An NO radical measuring method according to claim 1, wherein said luminol has a concentration of 1 µM to 1 mM.

7. An NO radical measuring method according to claim 1, wherein said solution is a perfusate.

8. An NO radical measuring method according to claim 7, wherein the reaction system pH is approximately 12.

9. An NO radical measuring method according to claim 1, wherein reaction system pH is approximately 12.

10. An NO radical measuring apparatus comprising:
    a flow cell containing a sample solution containing NO radicals and a mixed reaction solution containing a material selected from the group consisting of xanthine and xanthine oxidase, tert-butyl-hydroperoxide and hydrogen peroxide thereto and a material selected from the group consisting of isoluminol, AHEI, ABEI, ABEI-NCS, luciferin, Cypridina luciferin, CLA and MCLA and luminol; and
    a luminescence detecting portion disposed opposite to the flow cell for measuring NO radicals.

11. An apparatus according to claim 10, wherein said luminol has a concentration of 1 µM to 1 mM.

12. An apparatus according to claim 10, wherein said solution is a perfusate.

13. An apparatus according to claim 10, wherein said reaction solution pH is approximately 12.

14. An apparatus according to claim 12, wherein reaction solution pH is approximately 12.

* * * * *